United States Patent
Tockman et al.

(10) Patent No.: US 8,903,509 B2
(45) Date of Patent: Dec. 2, 2014

(54) SYSTEMS AND METHODS FOR STIMULATION OF VAGUS NERVE

(71) Applicant: Cardiac Pacemakers, Inc., St. Paul, MN (US)

(72) Inventors: Bruce A. Tockman, Scandia, MN (US); Brian D. Soltis, St. Paul, MN (US); Lili Liu, Maple Grove, MN (US); Eric F. Hammill, Ham Lake, MN (US)

(73) Assignee: Cardiac Pacemakers Inc., St. Paul, MN (US)

( * ) Notice: Subject to any disclaimer, the term of this patent is extended or adjusted under 35 U.S.C. 154(b) by 0 days.

(21) Appl. No.: 13/786,856

(22) Filed: Mar. 6, 2013

(65) Prior Publication Data
US 2013/0253624 A1    Sep. 26, 2013

Related U.S. Application Data

(60) Provisional application No. 61/613,763, filed on Mar. 21, 2012.

(51) Int. Cl.
*A61N 1/05* (2006.01)
*A61N 1/36* (2006.01)

(52) U.S. Cl.
CPC .......... *A61N 1/0558* (2013.01); *A61N 1/36053* (2013.01)
USPC .............................. 607/118; 607/116; 607/45

(58) Field of Classification Search
None
See application file for complete search history.

(56) References Cited

U.S. PATENT DOCUMENTS

| | | |
|---|---|---|
| 4,177,818 A | 12/1979 | De Pedro |
| 4,573,481 A | 3/1986 | Bullara |
| 4,590,946 A | 5/1986 | Loeb |
| 4,590,949 A | 5/1986 | Pohndorf |
| 4,602,624 A | 7/1986 | Naples et al. |
| 4,628,942 A | 12/1986 | Sweeney et al. |
| 4,740,170 A | 4/1988 | Lee et al. |
| 4,920,979 A | 5/1990 | Bullara |
| 4,940,065 A | 7/1990 | Tanagho et al. |
| 4,979,511 A | 12/1990 | Terry, Jr. |
| 5,031,621 A | 7/1991 | Grandjean et al. |
| 5,095,905 A | 3/1992 | Klepinski |

(Continued)

FOREIGN PATENT DOCUMENTS

| | | |
|---|---|---|
| EP | 0585553 A1 | 6/1993 |
| JP | 2005058456 A | 3/2005 |

(Continued)

OTHER PUBLICATIONS

International Search Report and Written Opinion Issued in PCT/US2009/063442, mailed Feb. 1, 2010, 11 pages.

(Continued)

*Primary Examiner* — Brian T Gedeon
(74) *Attorney, Agent, or Firm* — Faegre Baker Daniels LLP

(57) ABSTRACT

Described is a system for stimulating a target region of a vagus nerve from a location within an internal jugular vein. The system comprises a medical lead and an insulating element. The insulating element is formed from a flexible sheet of electrically insulative material, and is to be implanted within the internal jugular vein to insulate nerve structures proximate the vagus nerve from stimulation. The insulating sheath includes at least one window through which the electrical stimuli can be delivered to the target region of the vagus nerve.

17 Claims, 7 Drawing Sheets

(56) References Cited

U.S. PATENT DOCUMENTS

| | | | |
|---|---|---|---|
| 5,218,089 A | 6/1993 | Mariotti et al. | |
| 5,251,634 A | 10/1993 | Weinberg | |
| 5,259,394 A | 11/1993 | Bens | |
| 5,282,468 A | 2/1994 | Klepinski | |
| 5,324,322 A | 6/1994 | Grill, Jr. et al. | |
| 5,334,438 A | 8/1994 | Saugnac | |
| 5,351,394 A | 10/1994 | Weinberg | |
| 5,358,516 A | 10/1994 | Myers et al. | |
| 5,375,594 A | 12/1994 | Cueva | |
| 5,505,201 A | 4/1996 | Grill et al. | |
| 5,531,778 A | 7/1996 | Maschino et al. | |
| 5,674,272 A | 10/1997 | Bush et al. | |
| 5,689,877 A | 11/1997 | Grill et al. | |
| 5,755,766 A | 5/1998 | Chastain et al. | |
| 5,782,892 A | 7/1998 | Castle et al. | |
| 5,871,530 A | 2/1999 | Williams et al. | |
| 5,913,876 A | 6/1999 | Taylor et al. | |
| 5,964,702 A | 10/1999 | Grill et al. | |
| 6,038,479 A | 3/2000 | Werner et al. | |
| 6,051,017 A | 4/2000 | Loeb et al. | |
| 6,093,197 A | 7/2000 | Bakula et al. | |
| 6,174,329 B1 * | 1/2001 | Callol et al. | 623/1.34 |
| 6,178,349 B1 | 1/2001 | Kieval | |
| 6,249,708 B1 | 6/2001 | Nelson et al. | |
| 6,292,703 B1 | 9/2001 | Meier et al. | |
| 6,296,659 B1 | 10/2001 | Foerster | |
| 6,308,104 B1 | 10/2001 | Taylor et al. | |
| 6,308,105 B1 | 10/2001 | Duysens et al. | |
| 6,381,499 B1 | 4/2002 | Taylor et al. | |
| 6,423,080 B1 | 7/2002 | Gellman et al. | |
| 6,600,956 B2 | 7/2003 | Maschino et al. | |
| 6,725,096 B2 | 4/2004 | Chinn et al. | |
| 7,047,081 B2 | 5/2006 | Kuzma | |
| 7,054,692 B1 | 5/2006 | Whitehurst et al. | |
| 7,160,298 B2 | 1/2007 | Lawew et al. | |
| 7,212,867 B2 | 5/2007 | Venrooij et al. | |
| 7,502,650 B2 | 3/2009 | Kieval | |
| 7,536,227 B1 | 5/2009 | Poore et al. | |
| 7,561,923 B2 | 7/2009 | Libbus et al. | |
| 7,711,421 B2 | 5/2010 | Shafer et al. | |
| 7,749,273 B2 | 7/2010 | Cauthen, III et al. | |
| 7,807,925 B2 | 10/2010 | Zarembo | |
| 7,831,311 B2 | 11/2010 | Cross, Jr. et al. | |
| 7,891,085 B1 | 2/2011 | Kuzma et al. | |
| 7,925,352 B2 | 4/2011 | Stack et al. | |
| 7,925,358 B2 | 4/2011 | Beiden et al. | |
| 7,933,662 B2 | 4/2011 | Marshall et al. | |
| 7,957,817 B1 | 6/2011 | Gillespie et al. | |
| 7,974,706 B2 | 7/2011 | Moffitt et al. | |
| 7,996,092 B2 | 8/2011 | Mrva et al. | |
| 8,100,141 B2 | 1/2012 | Slupecki et al. | |
| 8,155,757 B1 | 4/2012 | Neisz et al. | |
| 8,244,372 B1 | 8/2012 | Zhulati et al. | |
| 8,295,948 B2 | 10/2012 | Barker et al. | |
| 8,326,418 B2 | 12/2012 | Sommer et al. | |
| 8,417,343 B2 | 4/2013 | Bolea et al. | |
| 8,452,406 B2 | 5/2013 | Arcot-Krishnamurthy et al. | |
| 8,483,845 B2 | 7/2013 | Sage | |
| 8,548,593 B2 | 10/2013 | Ternes et al. | |
| 8,639,355 B2 | 1/2014 | Soltis | |
| 2002/0116042 A1 | 8/2002 | Boling | |
| 2002/0128700 A1 | 9/2002 | Cross, Jr. | |
| 2003/0040785 A1 | 2/2003 | Maschino et al. | |
| 2003/0236558 A1 | 12/2003 | Whitehurst et al. | |
| 2004/0010303 A1 | 1/2004 | Bolea et al. | |
| 2004/0111139 A1 | 6/2004 | McCreery | |
| 2005/0209655 A1 | 9/2005 | Bradley et al. | |
| 2005/0234512 A1 | 10/2005 | Nakao | |
| 2005/0283246 A1 | 12/2005 | Cauthen, III et al. | |
| 2006/0030919 A1 | 2/2006 | Mrva et al. | |
| 2006/0122675 A1 | 6/2006 | Libbus et al. | |
| 2006/0190042 A1 | 8/2006 | Stone et al. | |
| 2006/0259078 A1 | 11/2006 | Libbus | |
| 2007/0071568 A1 | 3/2007 | Dorstewitz | |
| 2007/0083236 A1 | 4/2007 | Sikora et al. | |
| 2007/0100406 A1 | 5/2007 | Kollatschny et al. | |
| 2007/0118177 A1 | 5/2007 | Libbus et al. | |
| 2007/0142871 A1 | 6/2007 | Libbus et al. | |
| 2007/0173914 A1 | 7/2007 | Kollatschny | |
| 2007/0203556 A1 | 8/2007 | Rutten et al. | |
| 2007/0239243 A1 | 10/2007 | Moffitt et al. | |
| 2007/0255320 A1 | 11/2007 | Inman et al. | |
| 2008/0046058 A1 | 2/2008 | Cross et al. | |
| 2008/0051839 A1 | 2/2008 | Libbus et al. | |
| 2008/0058871 A1 | 3/2008 | Libbus et al. | |
| 2008/0058874 A1 | 3/2008 | Westlund et al. | |
| 2008/0058901 A1 | 3/2008 | Ternes et al. | |
| 2008/0086181 A1 | 4/2008 | Amurthur et al. | |
| 2008/0091255 A1 | 4/2008 | Caparso et al. | |
| 2008/0103407 A1 | 5/2008 | Bolea et al. | |
| 2008/0103545 A1 | 5/2008 | Bolea et al. | |
| 2008/0132987 A1 | 6/2008 | Westlund et al. | |
| 2008/0140092 A1 | 6/2008 | Stone et al. | |
| 2008/0172101 A1 | 7/2008 | Bolea et al. | |
| 2008/0177365 A1 | 7/2008 | Bolea et al. | |
| 2008/0177366 A1 | 7/2008 | Bolea et al. | |
| 2008/0183258 A1 | 7/2008 | Inman | |
| 2008/0195188 A1 | 8/2008 | Libbus et al. | |
| 2008/0234780 A1 | 9/2008 | Smith et al. | |
| 2008/0255613 A1 | 10/2008 | Kaiser et al. | |
| 2009/0048641 A1 | 2/2009 | Libbus | |
| 2009/0210042 A1 | 8/2009 | Kowalczewski | |
| 2009/0259260 A1 | 10/2009 | Bentley et al. | |
| 2009/0275997 A1 | 11/2009 | Faltys et al. | |
| 2009/0276024 A1 | 11/2009 | Bonde et al. | |
| 2009/0318961 A1 | 12/2009 | Stone et al. | |
| 2010/0023088 A1 | 1/2010 | Stack et al. | |
| 2010/0036451 A1 | 2/2010 | Hoffer | |
| 2010/0121405 A1 | 5/2010 | Ternes et al. | |
| 2010/0145221 A1 | 6/2010 | Brunnett et al. | |
| 2010/0168831 A1 | 7/2010 | Korivi et al. | |
| 2010/0211131 A1 * | 8/2010 | Williams et al. | 607/44 |
| 2010/0286553 A1 * | 11/2010 | Feler et al. | 600/554 |
| 2010/0305674 A1 | 12/2010 | Zarembo et al. | |
| 2010/0312320 A1 | 12/2010 | Faltys et al. | |
| 2010/0331938 A1 | 12/2010 | Sommer et al. | |
| 2011/0004281 A1 | 1/2011 | Jones | |
| 2011/0022142 A1 | 1/2011 | Barker et al. | |
| 2011/0040257 A1 | 2/2011 | Behymer et al. | |
| 2011/0060395 A1 | 3/2011 | Cantlon | |
| 2011/0172682 A1 | 7/2011 | Brady et al. | |
| 2011/0172701 A1 | 7/2011 | Wales et al. | |
| 2012/0022617 A1 | 1/2012 | Tockman et al. | |
| 2012/0035691 A1 | 2/2012 | Tockman et al. | |
| 2012/0065702 A1 | 3/2012 | Arcot-Krishnamurthy et al. | |
| 2012/0221087 A1 | 8/2012 | Parnis et al. | |
| 2013/0005169 A1 | 1/2013 | Soltis et al. | |
| 2013/0013045 A1 | 1/2013 | Soltis | |
| 2013/0172973 A1 | 7/2013 | Tockman et al. | |
| 2013/0253615 A1 | 9/2013 | Arcot-Krishnamurthy et al. | |
| 2014/0094888 A1 | 4/2014 | True, Kyle et al. | |

FOREIGN PATENT DOCUMENTS

| | | |
|---|---|---|
| JP | 2008526299 A | 7/2008 |
| WO | WO9929366 A1 | 6/1999 |
| WO | WO2004052176 A2 | 6/2004 |
| WO | WO2006093685 A1 | 9/2006 |
| WO | WO2007024164 A1 | 1/2007 |
| WO | WO2008088798 A1 | 7/2008 |
| WO | WO2008094349 A1 | 8/2008 |
| WO | WO2009020639 A1 | 2/2009 |
| WO | WO2009025817 A2 | 2/2009 |
| WO | WO2009100242 A2 | 8/2009 |
| WO | WO2011053766 A1 | 5/2011 |

OTHER PUBLICATIONS

International Search Report and Written Opinion Issued in PCT/US2010/026350, mailed Jun. 2, 2010.

International Search Report and Written Opinion Issued in PCT/US2011/049585, mailed Dec. 19, 2011.

International Search Report and Written Opinion Issued in PCT/US2012/044020, mailed Sep. 11, 2012, 9 pages.

(56) References Cited

OTHER PUBLICATIONS

International Search Report and Written Opinion issued in PCT/US2012/044028, mailed Oct. 1, 2012, 9 pages.
International Search Report and Written Opinion issued in PCT/US2012/071812, mailed Sep. 13, 2013, 12 pages.
International Search Report and Written Opinion issued in PCT/US2013/029306, mailed Jul. 18, 2013, 13 pages.
International Search Report and Written Opinion issued in PCT/US2014/015590, mailed May 28, 2014, 14 pages.
International Search Report and Written Opinion issued in PCT/US2011/020699, mailed Jul. 26, 2011, 24 pages.
International Search Report and Written Opinion issued in PCT/US2013/062560, mailed Dec. 17, 2014, 13 pages.
International Search Report and Written Opinion issued in PCT/US2013/062608, mailed Dec. 17, 2014, 13 pages.
Partial International Search Report issued in PCT/US2011/020699, mailed Mar. 24, 2011, 6 pages.
International Search Report and Written Opinion issued in PCT/US2013/077949, mailed Jun. 20, 2014, 15 pages.
Kirsch, Robert F. et al., "Restoration of Hand and Arm Function by Functional Neuromuscular Stimulation", Period covered: Jun. 1, 2001-Aug. 31, 2006, 71 pages.
International Preliminary Examination Report, Chapter II, issued in PCT/US2013/029306, completed Aug. 19, 2014, 16 pages.
Written Opinion of the International Preliminary Examining Authority issued in PCT/US2013/029306, mailed May 8, 2014, 6 pages.

* cited by examiner

SYSTEMS AND METHODS FOR STIMULATION OF VAGUS NERVE

CROSS-REFERENCE TO RELATED APPLICATION

This application claims priority to Provisional Application No. 61/613,763, filed Mar. 21, 2012, which is herein incorporated by reference in its entirety.

TECHNICAL FIELD

The disclosure relates to systems and methods for stimulating nerves. More particularly, the disclosure relates to systems and corresponding methods for stimulating a target region of a vagus nerve from a location within an internal jugular vein while avoiding stimulation of other proximate or adjacent structures.

BACKGROUND

The use of nerve stimulation for treating and controlling a variety of medical, psychiatric, and neurological disorders has seen significant growth over the last several decades, including for treatment of heart conditions, epilepsy, obesity, and breathing disorders, among others. For example, modulation of the autonomic balance with neural stimulation has been shown to be possible and have positive clinical benefits, such as protecting the myocardium from further remodeling and predisposition to fatal arrhythmias following a myocardial infarction (MI).

SUMMARY

In Example 1, a system for stimulating a target region of a vagus nerve from a location within an internal jugular vein. The system comprises a medical lead and an insulating element. The medical lead comprises a lead body extending from a proximal end to a distal end, a conductor extending within the lead body from the proximal end in a direction towards the distal end, and at least one electrode located on the lead body and operatively coupled to the conductor. The electrode is configured to transvascularly deliver an electrical stimuli to the target region of the vagus nerve from a location within the internal jugular vein. The insulating element includes an insulating sheath formed from a flexible sheet of electrically insulative material. The insulating sheath is configured to be implanted within the internal jugular vein and disposed about the lead and to insulate nerve structures proximate the vagus nerve from stimulation. The insulating sheath includes at least one window configured to be located between the lead and the target region of the vagus nerve through which the electrical stimuli can be delivered to the target region of the vagus nerve.

In Example 2, the system of Example 1, wherein the insulating element further includes a stent-like fixation member configured to expand from a collapsed delivery configuration to an expanded configuration, wherein in the expanded configuration, the stent-like fixation member is configured to secure the insulating sheath to an inner wall of the internal jugular vein.

In Example 3, the system of Example 2, wherein the stent-like fixation member is balloon expandable.

In Example 4, the system of Examples 2 or 3, wherein the stent-like fixation member is self-expandable.

In Example 5, the system of any of Examples 2-4, wherein the insulating sheath is radially disposed about the stent-like fixation member.

In Example 6, the system of any Examples 2-4, wherein the stent-like fixation member is radially disposed about the insulating sheath and the insulating sheath is attached to the stent-like fixation member.

In Example 7, the system of any of Examples 1-6, wherein the window comprises a plurality of perforations.

In Example 8, the system of any of Examples 1-7, wherein the window includes an electrically permeable material.

In Example 9, a system for stimulating a target region of a vagus nerve from a location within an internal jugular vein in a carotid sheath. The system comprises a medical lead and an insulating element. The medical lead comprises a lead body extending from a proximal end to a distal end, a conductor extending within the lead body from the proximal end in a direction towards the distal end, and at least one electrode located on the lead body and operatively coupled to the conductor. The electrode is configured to transvascularly deliver an electrical stimuli to the target region of the vagus nerve from a location within the internal jugular vein. The insulating element includes an insulating sheath formed from a flexible sheet of electrically insulative material configured to assume a generally tubular shape to surround at least a portion of the carotid sheath when implanted, and configured to surround the portion of the carotid sheath within which the lead electrode is positioned when implanted in order to insulate nerve structures proximate the vagus nerve from stimulation when the electrical stimuli is delivered by the lead electrode to the target region of the vagus nerve.

In Example 10, the system of Example 9, wherein the lead body comprises a pre-formed region configured to engage an inner wall of the internal jugular vein to secure and stabilize the lead body at a desired position within the internal jugular vein.

In Example 11, the system of either of Examples 9 or 10, wherein the insulating sheath comprises a first portion and a second portion, the first portion configured to surround the carotid sheath and the second portion configured to surround and contact an outer surface of the internal jugular vein in order to radially compress a localized region of the internal jugular vein.

In Example 12, the system of any of Examples 9-11, wherein the lead body comprises a pre-formed region configured to engage an inner wall of the localized region of the internal jugular vein to secure and stabilize the lead at a desired position within the internal jugular vein.

In Example 13, a method for stimulating a target region of a vagus nerve from a location within an internal jugular vein. The method comprises deploying an insulating element at a location proximate the target region of the vagus nerve, wherein the insulating element is at least partially radiopaque. Then, after deploying the insulating element, the method comprises advancing a medical lead including at least one electrode within the internal jugular vein while visualizing the deployed insulating element under fluoroscopy to determine a desired implantation position of the medical lead. The method further comprises positioning the medical lead with the at least one electrode positioned within the internal jugular vein at a location such that the at least one electrode is encircled by the insulating element, and operatively coupling the medical lead to a pulse generator to supply an electrical stimuli to the vagus nerve via the at least one electrode. The insulating element operates to electrically insulate nerves proximate the vagus nerve from exposure to the electrical stimuli.

In Example 14, the method of Example 13, wherein deploying the insulating element includes advancing the insulating element in a collapsed configuration within a delivery catheter to a location within the internal jugular vein proximate the target region of the vagus nerve, and releasing the insulating element from the delivery catheter thereby causing or allowing the insulating element to assume an expanded configuration in which the insulating element is secured against an inner wall of the internal jugular vein.

In Example 15, the method of either of Examples 13 or 14, wherein deploying the insulating element further includes orienting an electrically permeable window on the insulating element toward the vagus nerve, and wherein positioning the medical lead includes positioning the at least one electrode such that the electrical stimuli can be directed toward the vagus nerve through the window.

In Example 16, the method of any of Examples 13-15, wherein the insulating element includes an insulating sheath and a stent-like fixation member configured to transition from the collapsed configuration for delivery to the expanded configuration to secure the insulating element against the inner wall of the internal jugular vein.

In Example 17, the method of any of Examples 13-16, further comprising securing the lead to the insulating element such that the electrode of the medical lead is adjacent the target region of the vagus nerve.

In Example 18, the method of Example 13, wherein deploying the insulating element includes positioning at least a portion of the insulating element about the carotid sheath at a location within which the target region of the vagus nerve is located.

In Example 19, the method of either of Examples 13 or 18, wherein the insulating element includes a first portion and a second portion, and wherein deploying the insulating element includes positioning the first about the carotid sheath at a location within which the target region of the vagus nerve is located, and positioning the second portion about an outer surface of the internal jugular vein within the carotid sheath.

In Example 20, the method of Example 19, wherein the second portion of the insulating element is shaped to radially compress a region of the internal jugular vein, and wherein the lead body includes a pre-formed region defining a free dimension greater than a diameter of the compressed region of the internal jugular vein, and wherein positioning the medical lead includes positioning the pre-formed region so as to contact the compressed region of the internal jugular vein to inhibit longitudinal movement of the medical lead within the internal jugular vein.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

Figure 1:
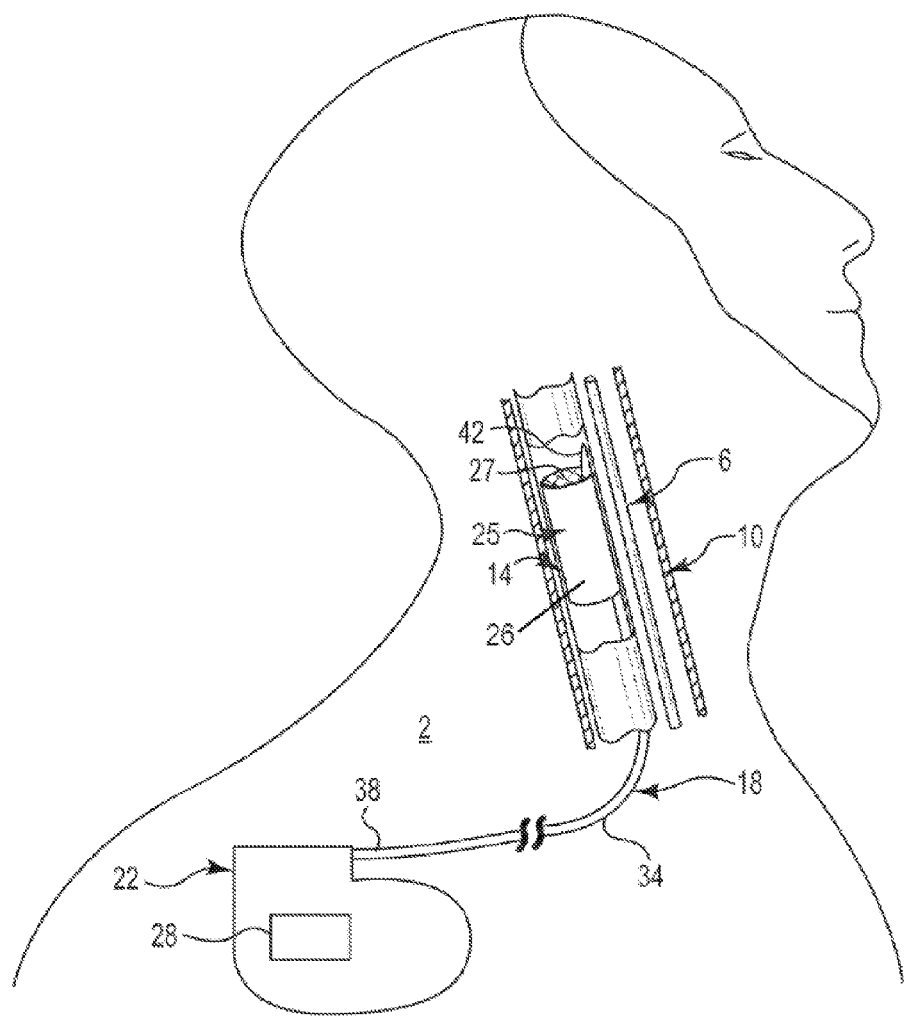
FIG. 1 is a schematic view of a system for stimulating a region of a patient's vagus nerve located within a carotid sheath according to an embodiment.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 2:
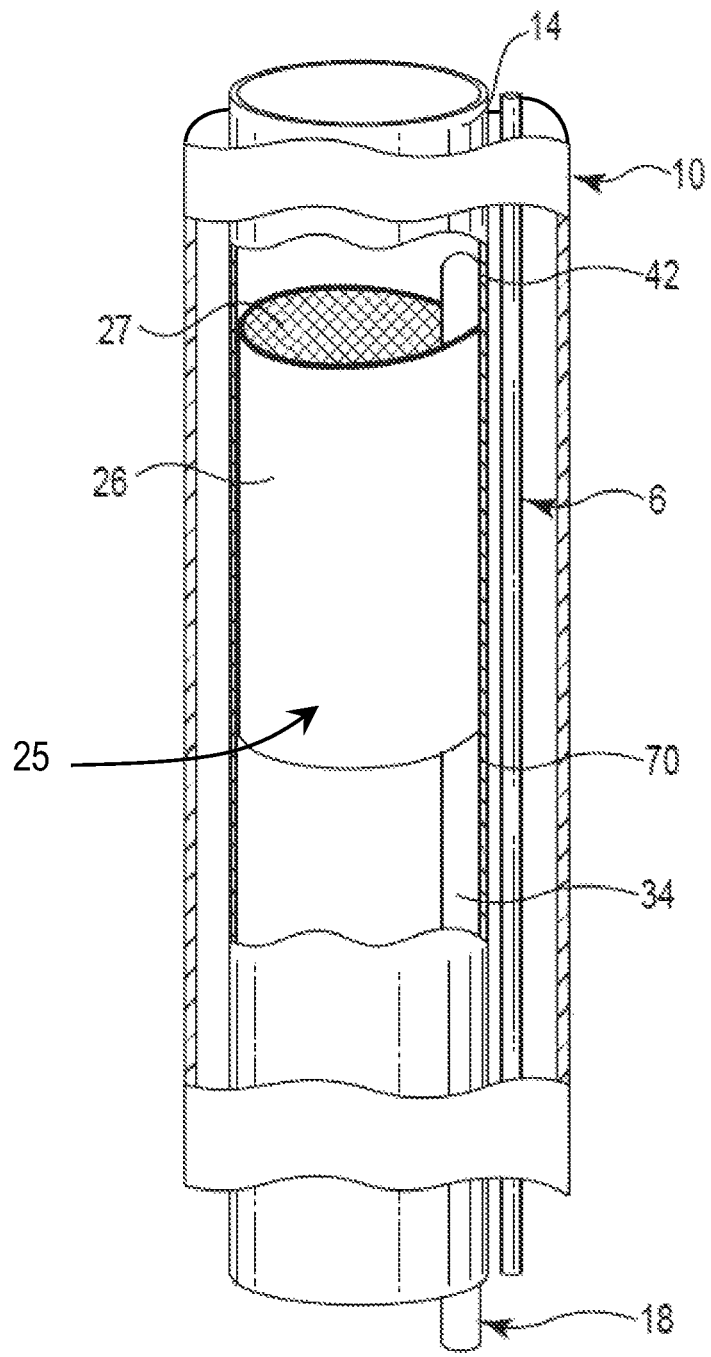
FIG. 2 is a close-up, schematic view of a portion of the system shown in FIG. 1.

FIG. 1 is a schematic illustration showing a system 2 for stimulating a region of a patient's vagus nerve 6 located within a carotid sheath 10 (shown in cross-section in FIG. 1), and FIG. 2 is a close-up, schematic view of a portion of the system 2. As is known, the carotid sheath 10 consists of multiple layers of fascia wrapping the common carotid artery (not shown), the internal jugular vein (IJV) 14, and the vagus nerve 6. As shown, the system 2 includes a lead 18, an implantable pulse generator 22, and an insulating element 25 including an insulating sheath 26 and a stent-like fixation member 27. In the illustrated embodiment, the lead 18 is coupled to the pulse generator 22, which includes a power source or battery 28. Additionally, the insulating element 25 is disposed about the lead 18, which is located within the IJV 14.

In the various embodiments, the system 2 is used to selectively stimulate the vagus nerve 6 for treating cardiac disease. As such, in various embodiments, the lead 18 includes electrodes (not shown in FIG. 1) that are electrically and operatively coupled to electronics and the power supply 28 of the pulse generator 22 to deliver electrical stimuli to the vagus nerve 6 when implanted. Additionally, as shown in FIG. 1, the insulating element 25 is disposed about the lead 18 when implanted and operates to inhibit undesired stimulation of nerves or muscle tissue outside the carotid sheath 10 or the IJV 14 by preventing electrical stimuli emitted from the aforementioned electrodes from being directed to such nerves or tissue. Thus, the insulating element 25 operates to confine the stimuli to selected contents of the carotid sheath 10, e.g., the vagus nerve 6. The system 2 thus facilitates providing optimal stimulation results by directing the stimuli towards the desired target—e.g., the vagus nerve 6—while minimizing conduction of energy to unintended anatomical structures.

In the illustrated embodiment, the insulating element 25 is disposed within the IJV 14. In various embodiments, the lead 18 and the insulating element 25 can be provided as separate elements that can be coupled together in situ after implantation. Alternatively, in various embodiments, the lead 18 and the insulating element 25 can be pre-assembled as a unitary element.

As shown in FIG. 1, the lead 18 includes an elongated, insulative lead body 34 extending from a proximal end 38 to a distal end 42. The lead 18 is coupled to the pulse generator 22 via a connector (not shown) located at the proximal end 38 of lead body 34. In various embodiments, the lead body 34 is generally flexible to allow for patient movement. In some embodiments, the lead body 34 can include one or more guide lumens to receive a guide member such as a guidewire or stylet in order to stiffen the lead body 34 for surgical implantation.

According to various embodiments, the lead 18 can include a plurality of conductors including individual wires, coils, or cables extending within the lead body 34 from the proximal end 38 in a direction towards the distal end 42 of the lead body 34. The conductors can be insulated with an insulator such as silicone, polyurethane, ethylene tetrafluoroethylene, or another biocompatible, insulative polymer. In one exemplary embodiment, the conductors have a co-radial design. In this embodiment, each individual conductor is separately insulated and then wound together in parallel to form a single coil. In another exemplary embodiment, the conductors have a co-axial, non-co-radial configuration. In various embodiments, the individual conductors may be single or multi-filar coil conductors. In still other embodiments, one or more of the conductors is a stranded cable conductor each routed through one of the aforementioned lumens in the lead body 34. In short, the various embodiments are not limited to any particular conductor configuration within the lead 18.

In various embodiments, the insulating element 25 can have a number of configurations that are able to surround the lead 18 while the lead 18 is located in the IJV 14. The configurations allow for selective stimulation of the vagus nerve 6 while substantially preventing undesired stimulation of nerves or other anatomical structures outside the carotid sheath 10. As shown in FIG. 1 and in FIG. 2, the insulating element 25 is disposed about the lead 18. In various embodiments, the insulating element 25 is configured to fit within the IJV 14 and substantially encircle the lead 18, with a window (not shown in FIG. 1 or 2) configured to be positioned adjacent to and aligned with the vagus nerve 6 to allow electrical stimulation pulses emitted from the lead 18 to be transmitted toward the vagus nerve 6. In alternative embodiments, as explained in further detail herein, however, the insulating element 25 can be configured to wrap around the outside of the IJV 14 or the carotid sheath 10, while the lead 18 is located within the IJV 14.

The insulating element 25 as shown includes stent-like fixation member 27 and insulating sheath 26. The insulating sheath 26 can be formed from a sheet of flexible, insulative biocompatible material. Suitable polymers that may be used for the insulating sheath 26 include, for example, silicone, polyurethane, polysiloxane urethane, ethylene tetrafluoroethylene (ETFE), polytetrafluoroethylene (PTFE), expanded PTFE (ePTFE), and expanded ultra-high-molecular-weight polyethylene (eUHMWPE), although others are also contemplated. Alternatively, the insulating sheath 26 could comprise a flexible sheet of material with an outer surface(s) or coating(s) of insulating material. Examples of such insulating material include, but are not limited to, those listed above that may be used for the insulating sheath 26. Depending upon the configuration of the assembled insulating element 25 and the method of assembling the insulating element 25, the desired flexibility of the material for the insulating sheath 26 may vary.

In one embodiment, the insulating sheath 26 can be made from or include a radiopaque material allowing the insulating sheath 26 to be visualized under fluoroscopy. For example, in one embodiment, the insulating sheath 26 can be loaded with a radiopaque filler material, e.g., bismuth subcarbonate or a comparable material that is visible under fluoroscopy but that does not materially impact the electrical insulating properties of the insulating sheath 26, thus imparting sufficient radiopacity to the insulating sheath 26 so that it can be visualized by the clinical staff under fluoroscopy during transvenous delivery of the insulating sheath 26.

As assembled, the insulating sheath 26 can be generally tubular-shaped or cylindrically-shaped. The insulating sheath 26 can also be tapered, such that, when assembled, the diameter of the insulating sheath 26 at one end is greater than the diameter at the opposite end. In various embodiments, the material forming the insulating sheath 26 may have a uniform or non-uniform cross-sectional thickness. In various embodiments, the insulating sheath 26 can be configured to exhibit a shape memory so as to be biased toward its final assembled (e.g., tubular) shape when implanted.

The insulating sheath 26 can include additional coatings, such as with non-thrombogenic materials or drug-eluting materials. The insulating sheath 26 can also be configured or made from such a material or materials so as to prevent tissue in-growth through the insulating sheath 26.

In one embodiment, and as shown in FIGS. 1 and 2, the insulating sheath 26 can be attached to the stent-like fixation member 27 which operates to hold the insulating element 25 in place within the IJV 14. The stent-like fixation member 27 can be constructed from a variety of biocompatible materials. In some embodiments, the stent-like fixation member 27 can be constructed from a wire mesh such as, for example a stainless steel or Nitinol™ wire mesh, among others. The stent-like fixation member 27 can be configured to transition from a collapsed configuration for delivery to the implant site within the IJV 14 to an expanded configuration, as shown in FIGS. 1 and 2. In one embodiment, the stent-like fixation member 27 can be balloon-expandable. In another embodiment, the stent-like fixation member 27 can be self-expanding. When in an expanded configuration, the stent-like fixation member 27 can expand to an outer diameter that is greater than an inner diameter of the IJV 14 such that it places a sufficient amount of a radial expansion force on the vessel walls of the IJV 14 so as to secure and stabilize the insulating sheath 26 in the IJV 14. The insulating sheath 26 can be configured to expand with the stent-like-fixation member 27.

In various embodiments, the stent-like fixation member 27 is made from a material that is radiopaque so that it can be visualized under fluoroscopy both during and after deployment of the stent-like fixation member 27. This radiopacity advantageously facilitates locating the stent-like fixation member 27 and, consequently, the insulating element 25, at a desired implantation location. In embodiments where the insulating sheath 26 and the stent-like fixation member 27 are deployed independently of and prior to deployment of the lead 18, the radiopacity of the stent-like fixation member 27 allows the clinician to use the stent-like fixation member 27 as a target for desired positioning of the lead 18.

Figure 3:
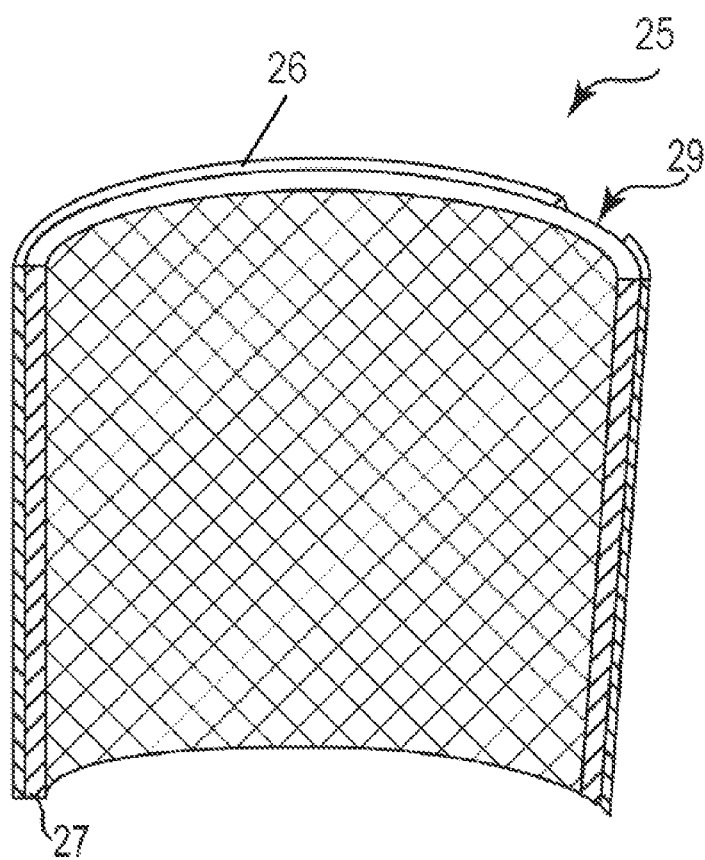
FIG. 3 is a partial cutaway view of one embodiment of an insulating element for use in the system of FIG. 1.

FIG. 3 is a partial cut-away view of the insulating element 25 of FIGS. 1 and 2. In the embodiment shown, the insulating sheath 26 is disposed about the stent-like fixation member 27, which operates to hold the insulating sheath 26 in place against an inner wall of the IJV when implanted. A window 29 (or opening) in the insulating sheath 26 is included and can be oriented toward the vagus nerve, or other target nerve, upon implantation. The window 29 can allow electrical stimuli or stimulation energy from electrodes on a lead within the insulating sheath 26 to be directed toward the vagus nerve, for example. Such a window 29 is included in embodiments in which the insulating element 25 is located within the carotid sheath 10.

The window 29 in the insulating sheath 26 can take on a variety of shapes or configurations. FIG. 3 shows an elongated window 29 in the form of a gap that extends the longitudinal length of the insulating sheath 26. Alternatively, the window 29 can extend less than the entire length of the insulating sheath 26. In another alternative embodiment, the window 29 can comprise a series of perforations that extend along the insulating sheath 26.

In another embodiment, the window 29 can be configured as a region of electrically permeable or porous, or electrically conductive, material through which electrical stimuli can be directed towards the vagus nerve 6. In such embodiments, the term "window" refers to a discontinuity in the electrical insulation forming the insulating sheath 26, rather than a region in which no material is present. Such an embodiment can have the additional advantage of providing a continuous sheath, with no physical discontinuity, which can enhance the structural integrity of the insulating sheath 26.

Figure 4:
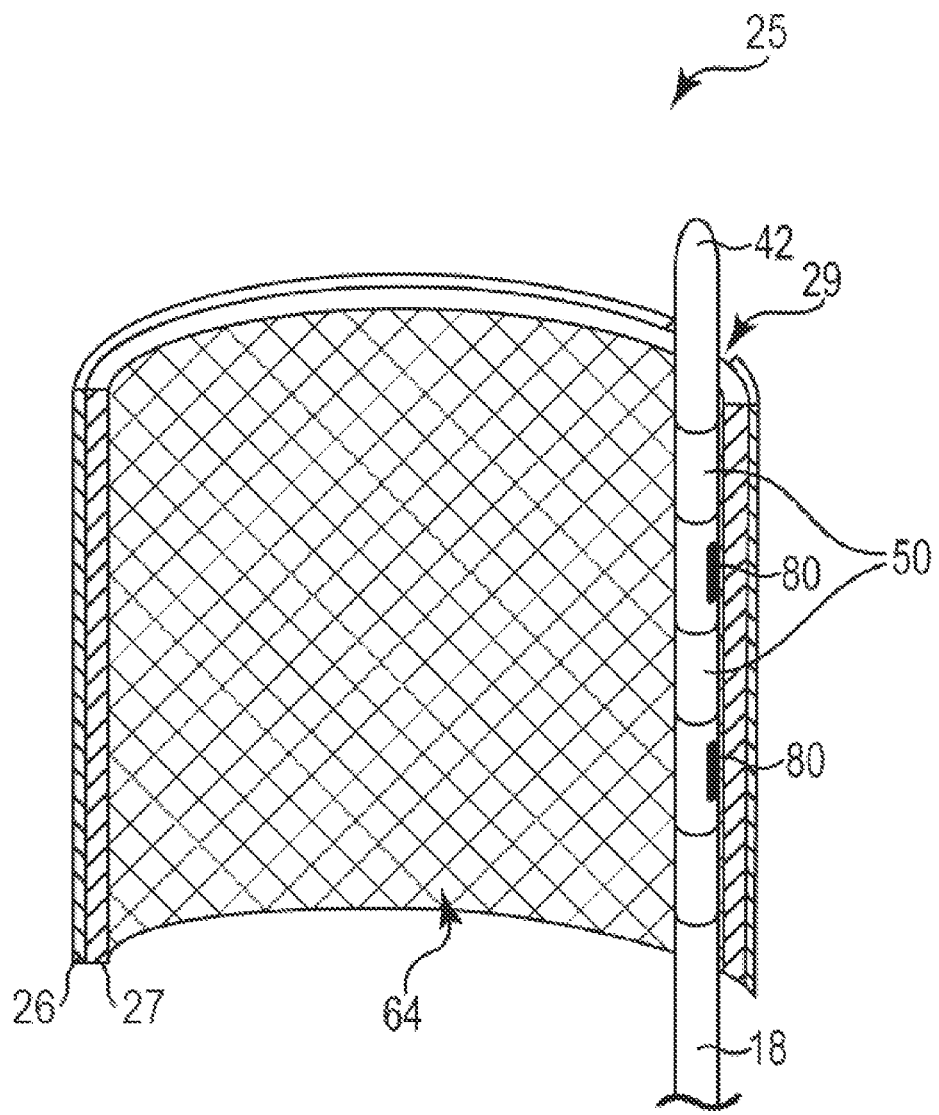
FIG. 4 is a partial cut away view of one embodiment of an insulating element with a lead for use in the system of FIG. 1.

FIG. 4 is a partial cut-away view of the insulating element 25 showing the lead 18 located on an inner surface 64 of the stent-like fixation member 27 proximate the window 29 (i.e., uninsulated portion) of the insulating sheath 26. As shown, the lead 18 includes a plurality of electrodes 50 (three are shown in FIG. 4) that will be oriented such that electrical stimuli will be directed radially outward through window 29. In various embodiments, the electrically active surface of at least one electrode 50 can be oriented in a direction towards window 29 and the region of the vagus nerve, or other target nerve structure, to be stimulated. In various embodiments, the electrodes 50 can be a ring or a partial ring electrode.

In some embodiments, the insulating element 25 and lead 18 can be connected and implanted together. Alternatively, the insulating element 25 and the lead 18 can be separate and implanted independently. If the insulating element 25 and the lead 18 are implanted separately, a means of attaching the components can be included. An exemplary attachment means is shown in FIG. 4. As illustrated, a first set of magnets 80 is located on the lead 18 and a corresponding second set of magnets (not shown) having an opposite charge from the first set of magnets 80 can be located on or embedded within the insulating sheath 26 and/or the stent-like fixation member 27 of the insulating element 25. In one embodiment, regions of the stent-like fixation member 27 can be made magnetic in lieu of the addition of separate magnets.

Other suitable attachment means are also contemplated. For example, the insulating sheath 26 and/or the stent-like fixation member 27 can be provided with a tacky or adhesive surface coating over a least a portion of its outer or inner surface to enhance frictional engagement with the lead body 34. In another embodiment, the insulating sheath 26 and/or the stent-like fixation member 27 can include one or more prongs or hooks configured to engage the lead body 34 in a cooperative manner. In yet another embodiment, the lead body 34 can include one or more projections such as prongs, hooks or tines that are configured to engage the insulating element 25. In various embodiments, the particular attachment mechanism employed is releasable to allow for detachment of the lead 18 from the insulating element 25 to allow for possible later removal of the lead 18.

Figure 5:
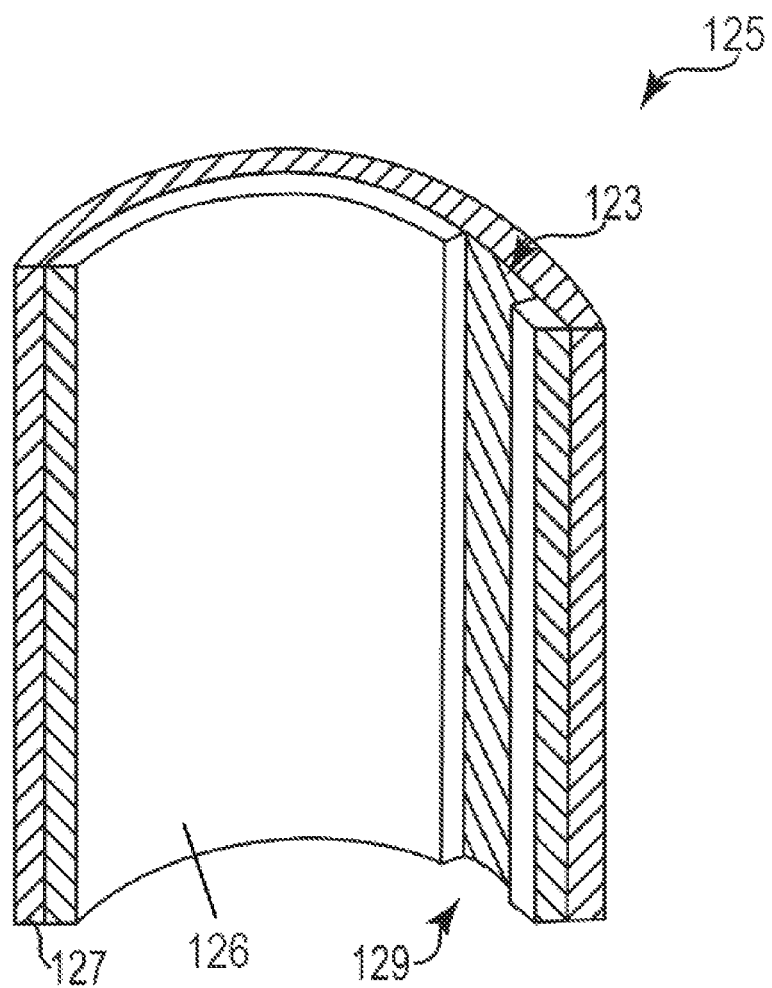
FIG. 5 is a partial cutaway view of one embodiment of an insulating element for use in the system of FIG. 1.

FIG. 5 shows another exemplary configuration of an alternative insulating element 125 including an insulating sheath 126 and a stent-like fixation member 127 coupled thereto. In the alternative embodiment shown, the stent-like fixation member 127 can be located radially outward from the insulating sheath 126, with the insulating sheath 126 being attached to an inner surface of the stent-like fixation member 127. In various embodiments, except as otherwise described herein, the insulating sheath 126 and the stent-like fixation member 127 can otherwise be configured substantially the same as or identically to the insulating sheath 26 or the stent-like fixation member 27, described herein with respect to FIG. 4.

Different methods of implantation of the described system 2 are possible. In one embodiment, the lead 18 can be delivered separately from insulating element 25, for example, in the manner discussed previously herein. In such an embodiment, the lead 18 can be connected in situ to the insulating element 25. Although reference is made herein to delivery techniques for deploying the insulating element 25, including the insulating sheath 26 and the stent-like fixation member 27, it is emphasized that substantially the same or identical techniques can be utilized to deploy the insulating element 125 including the sheath 126 and the stent-like fixation member 127.

In various embodiments, a delivery catheter can be used to advance the insulating element 25, including the insulating sheath 26 coupled to the stent-like fixation member 27, to a location adjacent an electrode region on lead 18. The insulating element 25 can be retained in a collapsed configuration during delivery by the delivery catheter, and then deployed from the delivery catheter. Before or during release of the insulating element 25 from the delivery catheter, the insulating element 25 can be rotated such that window 29 can be oriented toward the vagus nerve 6.

In various embodiments, as discussed previously, the insulating sheath 26 and/or the stent-like fixation member 27 is made radiopaque and thus visible under fluoroscopy, and are deployed independently of the lead 18. In these embodiments, the insulating element 25 is first deployed and secured at the desired implantation location and positioned within the IJV 14. Because it is visible under fluoroscopy, the insulating element 25 can advantageously provide a target for locating the electrodes 50 within the interior space defined by the deployed insulating sheath 26 and stent-like fixation member 27.

The lead 18 can be delivered to the target location using a variety of lead delivery techniques. In one embodiment, lead 18 can be advanced over a guidewire to the location within the IJV 14. In other embodiments, the lead 18 can be delivered using a guide catheter or a stylet.

In one embodiment, the insulating element 25, including the insulating sheath 26 and the stent-like fixation member 27, can be partially deployed from a delivery catheter and the lead 18 subsequently advanced within the same delivery catheter so that the electrodes 50 can be positioned within the interior of the partially-deployed sheath 26 and fixation member 27, and thus relatively close to the vessel wall 70 (FIG. 2) of the IJV 14. The partially deployed insulating element 25 can be rotated and repositioned until an optimal location for delivery of electrical stimuli through the window 29 to the vagus nerve 6 has been identified. In various embodiments, acute stimulation of the vagus nerve 6 can be used to determine whether placement of the lead 18 at a location and with respect to window 29 results in optimal stimulation of the vagus nerve 6 to produce a desired physiological effect. Physiological effects that can be produced and subsequently monitored include laryngeal muscle vibration from activation of the recurrent laryngeal nerve (RLN) (branch of the vagus nerve), heart rate, blood pressure, voice alteration or electroencephalogram signals. The lead 18 or insulating element 25 can be repositioned as necessary until an optimal position for stimulation resulting in a desired physiological effect is identified. Once the region of the vagus nerve 6 to be stimulated has been identified, the insulating element 25 can then be fully expanded at the implantation location, and the lead 18 fully deployed and secured within the insulating element 25.

Figure 6:
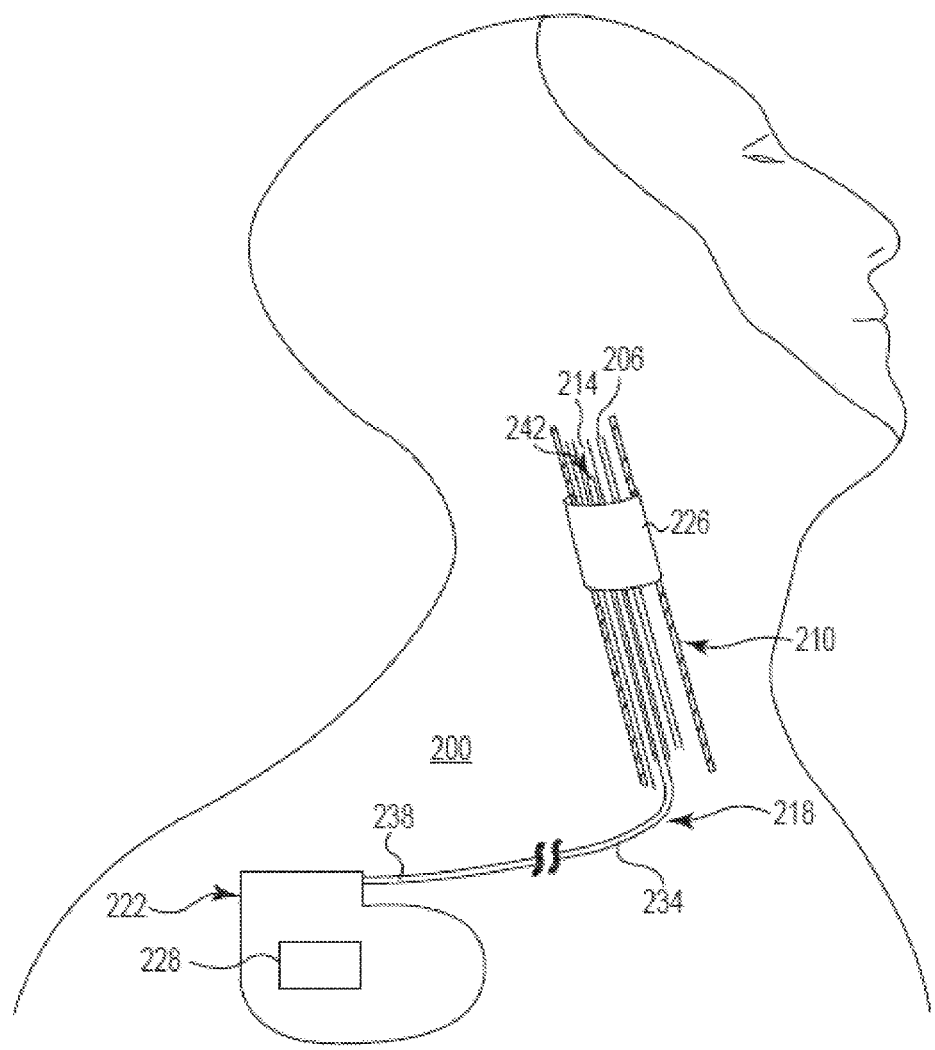
FIG. 6 is a schematic view of a system for stimulating a region of a patient's vagus nerve located within a carotid sheath according to an embodiment.

FIG. 6 is a schematic view of an alternative system 200 for stimulating a region of a patient's vagus nerve 206 located within a carotid sheath 210. System 200 includes a lead 218 (including lead body 234 having proximal end 238 and distal end 242), a pulse generator 222 (including power source 228), and an insulating element 226, which in the illustrated embodiment is a sheath made of electrically insulative material. Except as specifically discussed with respect to FIG. 6, the lead 218, the pulse generator 222 and the insulating element 226, and their components, can be substantially similar or identical to the lead 18, the pulse generator 22 and the insulating sheaths 26, 126 discussed elsewhere herein.

As shown, the lead 218 is located in an IJV 214, and is configured to generate therapeutic electrical stimuli for stimulating the vagus nerve 206. In addition, when fully implanted, the insulating element 226 is disposed about the carotid sheath 210 to substantially or completely encircle the contents of the carotid sheath 210 located within the axial length of the insulating element 226, including electrodes (not shown) on the lead 218.

The insulating element 226 can be implanted about the carotid sheath 210 either before or after delivery of the lead 218 to its implantation location within the IJV 214. In various embodiments, opposing edges of the insulating element 226 can include complementary suture holes that can be joined together using sutures. Other alternative means for joining the edges, are, however, also contemplated, and can include an adhesive, a hook and loop fastening mechanism, or other comparable joining techniques or features.

In one embodiment, the insulating element 226 can be formed of a material having shape memory or may be formed in such a way that the insulating element 226 returns to a predetermined tubular shape (i.e., is pre-coiled) after being deformed as it is disposed about the carotid sheath 210. In such embodiments, the insulating element 226 can be unrolled to fit around the carotid sheath 210 during implantation, and then allowed to spiral around itself to close.

The insulating element 226 can be implanted separately though a small incision formed in the skin of the neck. In one embodiment, a cut-down technique is employed by the clinicians to access the carotid sheath 210. After cutting down close to the carotid sheath 210, the clinician can then clear a space completely around the carotid sheath 210 in order to allow the insulating element 226 to be assembled around the carotid sheath 210. The insulating element 226 is then wrapped around the carotid sheath 210, and secured in place.

According to an exemplary implantation method, the lead 218 can be implanted in the IJV 214 according to methods previously described herein. In one embodiment, the insulating element 226 can include radiopaque markers or be made from a radiopaque material in order to be visible using fluoroscopy. The insulating element 226 being radiopaque can assist a physician during subsequent implantation of the lead 218 within a portion of the carotid sheath 210 surrounded by the insulating element 226, for example, by providing a target, visualized under fluoroscopy, for locating a desired implantation location for the electrodes (not shown) on the lead 218.

Figure 7:
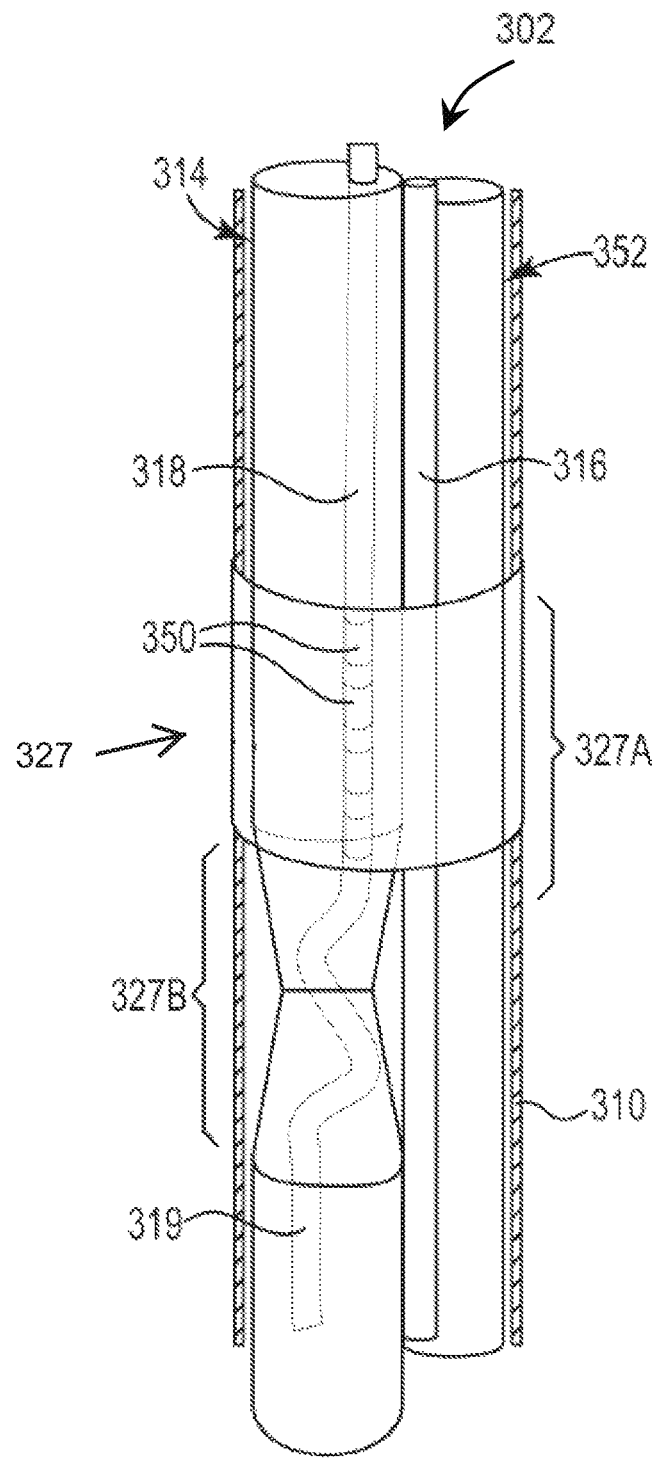
FIG. 7 is a schematic view of a portion of a system for stimulating a region of a patient's vagus nerve located with a carotid sheath according to an embodiment.

FIG. 7 is a schematic view of a portion of another alternative system 302 for stimulating a region of a patient's vagus nerve 316 located within a carotid sheath 310. A portion of the contents of the carotid sheath 310 is shown, including a carotid artery 352, IJV 314 and the vagus nerve 316. As shown, the system 302 includes a lead 318 (illustrated in phantom outline) and an insulating element 327. In the illustrated embodiment, the lead 318 is located within the IJV 314. The lead 318 includes a pre-formed region 319, and a plurality of electrodes 350 located distal to the pre-formed region 319. The electrodes 350 are configured to provide electrical stimuli to the vagus nerve 316. The pre-formed region 319 is configured to assist in fixating the lead 318 by engaging an interior surface of the IJV 314 when implanted. Although in the illustrated embodiment the pre-formed region 319 takes the form of a three-dimensional spiral, in other embodiments the pre-formed region 319 of the lead 318 can include a variety of pre-formed shapes including two dimensional shapes or other three-dimensional shapes.

As further shown in FIG. 7, the insulating element 327 has two longitudinal portions 327A and 327B. The portion 327A is configured to be implanted to surround the portion of the carotid sheath 310 in which the electrodes 350 of lead 318 are located. Additionally, the second portion 327B of insulating element 327 configured to be wrapped around the IJV 314 itself, as illustrated in FIG. 7. As further shown, the first and second portions 327A, 327B have different diameters, with the second portion 327B having a smaller diameter than the first portion 327A. In addition, in various embodiments and as shown in FIG. 7, the second portion 327B can also include a tapered profile so as to include a reduced-diameter portion that has a diameter smaller than the natural diameter of the IJV 314. This reduced-diameter portion operates to locally reduce the diameter of the IJV 314 to a dimension smaller than the free diameter of the spiral-shaped pre-formed region 319 of the lead 318, which in the illustrated embodiment is positioned above the reduced-diameter portion of the portion 327B when implanted. In this arrangement, the interaction of the pre-formed region 319 of the lead 318 and the IJV 314 within the reduced diameter portion of the portion 327B operates to limit or inhibit motion (e.g., retrograde motion) of the lead 318 within the IJV 314.

The lead 318 and insulating element 327 can be implanted using methods as described previously herein. For example, the lead 318 can be delivered using known transvenous lead delivery techniques as discussed previously. As with other embodiments, the insulating element 327 can be made from or include a radiopaque material, such that when the insulating element 327 is positioned prior to delivering the lead 318, visualization of the insulating sheath 327 under fluoroscopy can facilitate positioning the lead 318 at the desired implantation location.

In various embodiments, the insulating element portion 327A can be positioned and secured around the carotid sheath 310 in the same manner described elsewhere with respect to the insulating element 226. Once the portion 327A is positioned, the insulating element portion 327B can be implanted between tissue or layers of fascia of the carotid sheath 310 and placed around the IJV 314. For example, if desired, a trocar can be used to separate fibers or tissue in order to implant the insulating element portion 327B.

In another alternative embodiment, the insulating element portion 327A is omitted, and only the portion 327B configured to be disposed about the IJV 314 is utilized.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as they fall within the scope of the claims, together with all equivalents thereof.

We claim:

1. A system for stimulating a target region of a vagus nerve from a location within an internal jugular vein, the system comprising:
   a medical lead comprising a lead body extending from a proximal end to a distal end, a conductor extending within the lead body from the proximal end in a direction towards the distal end, and at least one electrode located on the lead body and operatively coupled to the conductor, the electrode configured to transvascularly deliver an electrical stimuli to the target region of the vagus nerve from a location within the internal jugular vein; and
   an insulating element including an insulating sheath formed from a flexible sheet of electrically insulative material, wherein the insulating sheath is configured to be implanted within the internal jugular vein and disposed about the lead and to insulate nerve structures proximate the vagus nerve from stimulation, wherein the insulating element further comprises a stent-like fixation member configured to expand from a collapsed delivery configuration to an expanded configuration, wherein in the expanded configuration, the stent-like fixation member is configured to secure the insulating sheath to an inner wail of the internal jugular vein, and wherein the insulating sheath includes at least one window configured to be located between the lead and the target region of the vagus nerve through. which the electrical stimuli can be delivered to the target region of the vagus nerve.

2. The system of claim 1, wherein the stent-like fixation member is balloon expandable.

3. The system of claim 1, wherein the stent-like fixation member is self-expandable.

4. The system of claim 1, wherein the insulating sheath is radially disposed about the stent-like fixation member.

5. The system of claim 1, wherein the stent-like fixation member is radially disposed about the insulating sheath and the insulating sheath is attached to the stent-like fixation member.

6. The system of claim 1, wherein the window comprises a plurality of perforations.

7. The system of claim 1, wherein the window includes an electrically permeable material.

8. A system for stimulating a target region of a vagus nerve from a location within an internal jugular vein in a carotid sheath, the system comprising:
   a medical lead comprising a lead body extending from a proximal end to a distal end, a conductor extending within the lead body from the proximal end in a direction towards the distal end, and at least one electrode located on the lead body and operatively coupled to the conductor, the electrode configured to transvascularly deliver an electrical stimuli to the target region of the vagus nerve from a location within the internal jugular vein; and
   an insulating element including an insulating sheath formed from a flexible sheet of electrically insulative material configured to assume a generally tubular shape to surround at least a portion of the carotid sheath when implanted, and configured. to surround the portion of the carotid sheath within which the lead electrode is positioned when implanted in order to insulate nerve structures proximate the vagus nerve from stimulation when the electrical stimuli is delivered by the lead electrode to the target region of the vagus nerve, wherein the insulating sheath comprises a first portion and a second portion, the first portion configured to surround the carotid sheath and the second portion configured to surround and contact an outer surface of the internal jugular vein in order to radially compress a localized region of the internal jugular vein.

9. The system of claim 8, wherein the lead body comprises a pre-formed region configured to engage an inner wall of the internal jugular vein to secure and stabilize the lead body at a desired position within the internal jugular vein.

10. The system of claim 8, wherein the lead body comprises a pre-formed region configured to engage an inner wall of the localized region of the internal jugular vein to secure and stabilize the lead at a desired position within the internal jugular vein.

11. A method for stimulating a target region of a vagus nerve from a location within an internal jugular vein, the method comprising:
   deploying an insulating element at a location proximate the target region of the vagus nerve, wherein the insulating element is at least partially radiopaque, wherein the insulating element includes a first portion and a second portion, and wherein deploying the insulating element includes positioning the first portion about the carotid sheath at a location within which the target region of the vagus nerve is located, and positioning the second portion about an outer surface of the internal jugular vein within the carotid sheath;
   after deploying the insulating element, advancing a medical lead including at least one electrode within the internal jugular vein while visualizing the deployed insulating element under fluoroscopy to determine a desired implantation position of the medical lead;
   positioning the medical lead with the at least one electrode positioned within the internal jugular vein at a location such that the at least one electrode is encircled by the insulating element; and
   operatively coupling the medical lead to a pulse generator to supply an electrical stimuli to the vagus nerve via the at least one electrode,
   wherein the insulating element operates to electrically insulate nerves proximate the vagus nerve from exposure to the electrical stimuli.

12. The method of claim 11, wherein deploying the insulating element includes advancing the insulating element in a collapsed configuration within a delivery catheter to a location within the internal jugular vein proximate the target region of the vagus nerve, and releasing the insulating element from the delivery catheter thereby causing or allowing the insulating element to assume an expanded configuration in which the insulating element is secured against an inner wall of the internal jugular vein.

13. The method of claim 12, wherein deploying the insulating element further includes orienting an electrically permeable window on the insulating element toward the vagus nerve, and wherein positioning the medical lead includes positioning the at least one electrode such that the electrical stimuli can be directed toward the vagus nerve through the window.

14. The method of claim 12, wherein the insulating element includes an insulating sheath and a stent-like fixation member configured to transition from the collapsed configuration for delivery to the expanded configuration to secure the insulating element against the inner wall of the internal jugular vein.

15. The method according to claim 11, further comprising securing the lead to the insulating element such that the electrode of the medical lead is adjacent the target region of the vagus nerve.

16. The method according to claim 11, wherein deploying the insulating element includes positioning at least a portion of the insulating element about the carotid sheath at a location within which the target region of the vagus nerve is located.

17. The method of claim 11, wherein the second portion of the insulating element is shaped to radially compress a region of the internal jugular vein, and wherein the lead body includes a pre-formed region defining a free dimension greater than a diameter of the compressed region of the internal jugular vein, and wherein positioning the medical lead includes positioning the pre-formed region so as to contact the compressed region of the internal jugular vein to inhibit longitudinal movement of the medical lead within the internal jugular vein.

* * * * *